(12) United States Patent
Collins et al.

(10) Patent No.: US 6,872,734 B2
(45) Date of Patent: Mar. 29, 2005

(54) USE OF TIAGABINE FOR TREATMENT OF DIABETIC NEUROPATHY AND MIGRAINE

(75) Inventors: Stephen D. Collins, Flemington, NJ (US); Roger L. Deaton, Wadsworth, IL (US); William J. Giardina, Libertyville, IL (US); Adrienne L. Gilbert, Vernon Hills, IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 10/041,782

(22) Filed: Oct. 18, 2001

(65) Prior Publication Data

US 2002/0103236 A1 Aug. 1, 2002

Related U.S. Application Data

(60) Provisional application No. 60/242,151, filed on Oct. 20, 2000.

(51) Int. Cl.[7] .............................................. A61K 31/445
(52) U.S. Cl. ....................................................... 514/326
(58) Field of Search ......................................... 514/326

(56) References Cited

U.S. PATENT DOCUMENTS

| | | |
|---|---|---|
| 4,383,999 A | 5/1983 | Bondinell et al. ........... 424/266 |
| 4,514,414 A | 4/1985 | Bondinell et al. ........... 514/422 |
| 5,010,090 A | 4/1991 | Gronvald et al. ........... 514/326 |

FOREIGN PATENT DOCUMENTS

| | | | |
|---|---|---|---|
| WO | 99/37302 | 7/1999 | ......... A61K/31/445 |

OTHER PUBLICATIONS

Attal, N., Douleur et Analgesis, 12/3:231–241 (Abstract) (1999).

Freitag et al., Headache Quarterly, 11/2:133–134 (abstract) (2000).

Giardina et al., "An Evaluation of the GABA Uptake Blocker Tiagabine in Animal Models of Neuropathic and Nociceptive Pain," Drug Development Research 44:106–113 (1998).

Krogsgaard–Larsen, "Inhibitors of the GABA Uptake Systems", Molecular & Cellular Biochemistry, vol. 31, 1980, p. 105–121.

Ross, E. L., Neurology, 55/5 Suppl. 1:S41–S46 (2000).

Yunger et al., "Novel Inhibitors of γ–Amniobutyric Acid (GABA) Uptake : Anticonvulsant Actions in Rats and Mice", The Journal of Pharmacology and Experimental Therapeutics., Vol 228, No. 1, 1984, p. 109 et seq.

*Primary Examiner*—Rebecca Cook
(74) *Attorney, Agent, or Firm*—Portia Chen; Michael J. Ward

(57) ABSTRACT

(R)-N-[4,4-Bis(3-methyl-2-thienyl)-3-butenyl]nipecotic acid and salts thereof are effective GABA uptake inhibitory compounds and exert pharmacological effects on pain associated with diabetic neuropathy and migraine.

2 Claims, 3 Drawing Sheets

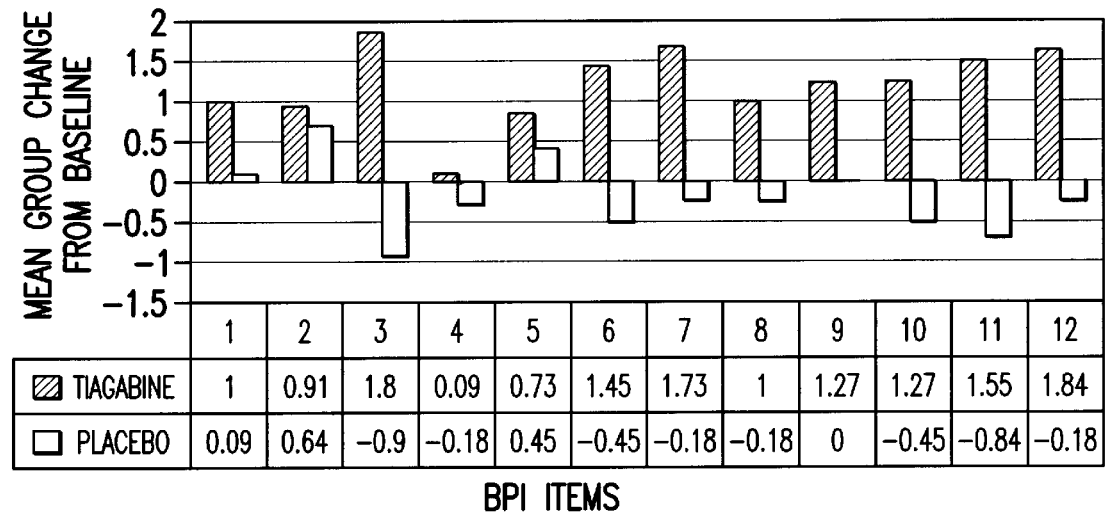

BPI ITEMS

1. WORST PAIN INTENSITY IN LAST 24 HOURS.
2. AVERAGE PAIN INTENSITY SINCE LAST VISIT.
3. PERCENTAGE OF RELIEF IN LAST 24 HOURS. (DIVIDED BY 10)
4. PAIN INTENSITY RIGHT NOW.
5. LEAST PAIN INTENSITY IN LAST 24 HOURS.
6. INTERFERENCE WITH GENERAL ACTIVITY IN LAST 24 HOURS.
7. INTERFERENCE WITH MOOD IN LAST 24 HOURS.
8. INTERFERENCE WITH WALKING ABILITY IN LAST 24 HOURS.
9. INTERFERENCE WITH NORMAL WORK IN LAST 24 HOURS.
10. INTERFERENCE WITH RELATIONS WITH OTHER PEOPLE IN LAST 24 HOURS.
11. INTERFERENCE WITH SLEEP IN LAST 24 HOURS.
12. INTERFERENCE WITH ENJOYMENT OF LIFE IN LAST 24 HOURS.

1. Please rate your pain by circling the one number that best describes your pain at its <u>worst</u> in the last 24 hours.

| 0 | 1 | 2 | 3 | 4 | 5 | 6 | 7 | 8 | 9 | 10 |
|---|---|---|---|---|---|---|---|---|---|---|
| No Pain | | | | | | | | | | Pain as bad as you can imagine |

2. Please rate your pain by circling the one number that best describes your pain on the <u>average</u> since the last visit.

| 0 | 1 | 2 | 3 | 4 | 5 | 6 | 7 | 8 | 9 | 10 |
|---|---|---|---|---|---|---|---|---|---|---|
| No Pain | | | | | | | | | | Pain as bad as you can imagine |

3. In the last 24 hours, how much relief have pain treatments or medications provided? Please circle the one percentage that most shows how much relief you have received.

| 0% | 10% | 20% | 30% | 40% | 50% | 60% | 70% | 80% | 90% | 100% |
|---|---|---|---|---|---|---|---|---|---|---|
| No Pain | | | | | | | | | | Pain as bad as you can imagine |

4. Please rate your pain by circling the one number that tells how much pain you have <u>right now</u>.

| 0 | 1 | 2 | 3 | 4 | 5 | 6 | 7 | 8 | 9 | 10 |
|---|---|---|---|---|---|---|---|---|---|---|
| No Pain | | | | | | | | | | Pain as bad as you can imagine |

5. Please rate your pain by circling the one number that best describes your pain at its <u>least</u> in the last 24 hours.

| 0 | 1 | 2 | 3 | 4 | 5 | 6 | 7 | 8 | 9 | 10 |
|---|---|---|---|---|---|---|---|---|---|---|
| No Pain | | | | | | | | | | Pain as bad as you can imagine |

Figure 2B
Circle the one number that describes how, during the past 24 hours, pain has interfered with your:
6. General Activity
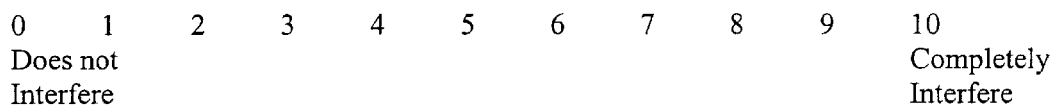
7. Mood
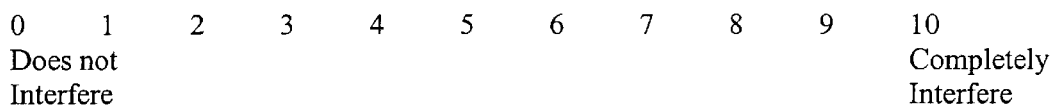
8. Walking Ability
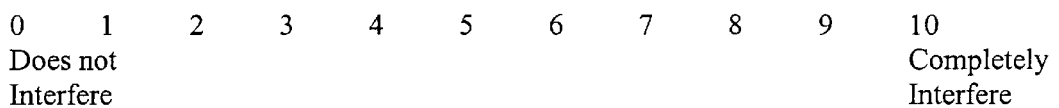
9. Normal work (includes both work outside the home or housework)
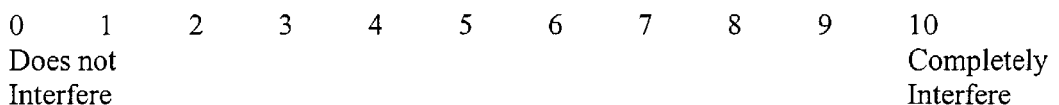
10. Relations with other people
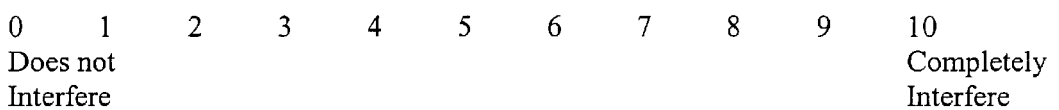
11. Sleep
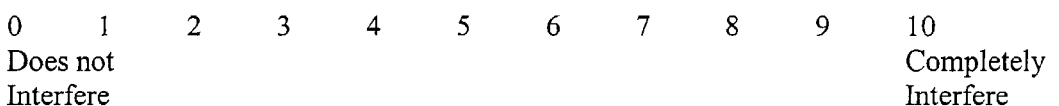
12. Enjoyment of Life

USE OF TIAGABINE FOR TREATMENT OF DIABETIC NEUROPATHY AND MIGRAINE

This application claims priority to U.S. provisional application Ser. No. 60/242,151, filed Oct. 20, 2000.

BACKGROUND OF THE INVENTION

In the last two decades, intensive pharmacological research concerning gamma-aminobutyric acid (GABA), a neurotransmitter in the central nervous system, has taken place.

Compounds which increase GABA activity are useful in the treatment of anxiety, epilepsy and muscular and movement disorders. Furthermore, these compounds can be used as sedatives.

In U.S. Pat. Nos. 4,383,999 and 4,514,414 (Smithkline Beckman Corporation) some derivatives of N-(4-phenylbuten-3-yl)azaheterocyclic carboxylic acids which have, furthermore, inter alia, phenyl, 4-fluorophenyl, cyclohexyl or thienyl in the 4-position, are described. It is stated therein that the compounds are useful as inhibitors of GABA uptake.

According to J. Pharm. Exp. Therap., 228 (1984), 109 et seq., N-(4,4-diphenyl-3 butenyl)nipecotic acid (designated SK&F 89976A). N-(4,4-diphenyl-3-butenyl)guvacine (designated SK&F 100330A), N-(4,4-diphenyl-3-butenyl)-B-homoproline (designated SK&F 100561) and N-(4-phenyl-4-(2-thienyl)-3-butenyl)nipecotic acid (designated SK&F 100604J) are active inhibitors of GABA uptake.

It is further well recognized in the art that B-homoproline, nipecotic acid and guvacme are biological equivalents, at least as far as their GABA-like effects regards.

See for example Progress in Medicinal Chemistry 21, 67–120 (1985); ed. Ellis West; Elsevier Science Publishers; Molecular and Cellular Biochemistry 31, 105–121 (1980), and J. Pharm. Exp. Therap., 228 (1984), 109 et seq.

U.S. Pat. No. 5,010,090 teaches the use of N-(Butenyl Substituted) Aza-Hetreocyclic Carboxylic Acids as exhibiting GABA uptake inhibitory properties. In particular, N-[4,4Bis(3-methyl-2-thienyl)-3-butenyl]nipecotic acid and salts thereof are effective GABA uptake inhibitory compounds. These compounds have been found to be effective in the treatment of chronic pain.

A study evaluated tiagabine HCl in animal models of neuropathic and nociceptive pain. An Evaluation of the GABA Uptake Blocker Tiagabine in Animal Models of Neuropathic and Nociceptive Pain, A. Giardina et al. The study did not evaluate the effects of tiagabine HCl in treating humans or pain associated with diabetic polyneuropathy and migraine.

BRIEF DESCRIPTION OF THE DRAWINGS

FIG. 1 depicts a list of the BPI items and the Change in Brief Pain Inventory in the Double-blind study comparing tiagabine XR to placebo. The ratings for the BPI items may range from 0–10 (except 0%–100% for item 3). The results indicated that tiagabine XR improved scores in all 12 parameters and the positive effect of tiagabine XR was statistically significant in items 3 and 11. Mean changes in the two scores are displayed as improvements from baseline such as that a positive change reflects improvement and a negative change reflects worsening.

FIG. 2.A. is a listing of the BPI items 1 through 5 asked during the double-blind study. FIG. 2.B. is a listing of BPI items 6 through 12 asked during the double-blind study.

DETAILED DESCRIPTION OF THIS INVENTION

It has been found that (R)-N-[4,4-Bis(3-methyl-2-thienyl)-3-butenyl]nipecotic acid and salts thereof are effective GABA uptake inhibitory compounds and exert pharmacological effects on pain associated with diabetic neuropathy and migraine. (R)-N-[4,4-Bis(3-methyl-2-thienyl)-3-butenyl]nipecotic acid hydrochloride (Tiagabine HCl, (Gabitril®) is sold commercially as an anti-epileptic. It is to be understood that isomers, including enantiomers, are included within the scope of this invention. U.S. Pat. No. 5,010,090 teaches the synthesis and use of N-(Butenyl Substituted) Aza-Hetreocyclic Carboxylic Acids as exhibiting GABA uptake inhibitory properties. U.S. Pat. No. 5,010,090 is hereby entirely incorporated by reference.

An extended release formulation of (R)-N-[4,4-Bis(3-methyl-2-thienyl)-3butenyl]nipecotic acid hydrochloride (Tiagabine XR) (Formula G, 7507-9; Abbott Laboratories, IL.) was used for the treatment of pain associated with diabetic polyneuropathy. Tiagabine XR formulations useful include tiagabine and high molecular weight polyethylene oxide formulations that are exemplified in WO 99/37302, which published Jul. 29, 1999. WO 99/37302 is hereby fully incorporated by reference.

A single-center pilot study with an initial Open-Label Phase, followed by a randomized, double-blind, placebo-controlled, two-period, crossover phase, for subjects who demonstrated a reduction in their pain during the Open-Label Phase. The Open-Label Phase consisted of a Screening Period of up to 14 days and an up to 6-week Dose-Evaluation Period. The Double-Blind Phase consisted of two 1 to 5 week(s) treatment periods, each preceded by a 1-week Washout Period. The actual duration of the study was to have varied from subject to subject and was to range from 9 to 19 weeks for those who qualified for the Double-Blind Phase, depending on the maximum tolerated dose (MTD) of tiagabine XR established during the Open-Label Phase.

The Open-Label Phase study evaluated 35 patients with painful diabetic polyneuropathy. Patients were initially titrated to their maximum tolerated dose of an extended release formulation of tiagabine hydrochloride (tiagabine XR) (Abbott Laboratories, Abbott Park, Ill.) and were assessed by the Brief Pain Inventory (BPI). the BPI is hereby incorporated by reference. Patients successfully tolerating a daily dose of at least 12 mg (max: 60 mg) who demonstrated pain relief of at least three units on the worst/average pain items of the BPI were randomized, washed out, and re-titrated to their previously tolerated dose in a two-period, double-blind, placebo-controlled crossover phase.

Males or non-pregnant, non-lactating females at least 18 years of age, diagnosed with stable chronic pain for at least 3 months, who met diagnostic criteria for generalized, symmetrical, painful diabetic polyneuropathy and had a pain rating of 3 units or higher on the worst pain item of the BPI at Visit 1 were eligible for study participation. FIG. 2 provides a listing of the BPI items. Additionally, subjects who were on a fixed-schedule analgesic regimen must have been on a stable dose for 14 days prior to Visit 1. Subjects with a current seizure disorder or with a significant neurologic or psychiatric illness or impairment were not eligible for study participation.

Subjects entering the Dose-Evaluation started tiagabine XR dosing at 12 mg/day for 1 week. Each week thereafter the dose of tiagabine XR was increased by 12 mg/day up to a maximum of 60 mg/day. The Dose-Evaluation Period ended after 1 week of stable dosing at the MTD. Subjects who demonstrated a reduction from Visit 1 of at least 2 units in either the worst pain or average pain items of the BPI and met all other randomization criteria entered the Double-Blind Phase.

Subjects who met the criteria for entry into the Double-Blind Phase were randomly assigned in equal numbers to one of two treatment sequences:

Sequence Group 1: Placebo (Treatment Period I): tiagabine XR (Treatment Period II)

Sequence Group 2: Tiagabine XR (Treatment Period 1): placebo (Treatment Period II)

The Double-Blind Phase consisted of two equal-length treatment periods; each preceded by a 1-week Washout Period. Throughout the study, the BPI was used to assess the subject's pain.

Seventeen subjects completed the open-label dose evaluation period. Five did not identify sufficient pain reduction (3 units in either the worst pain or average pain items of the BPI) to qualify for randomization. One declined for personal reasons. All 11 randomized subjects completed the Double-Blind Phase of the study.

Statistically significant differences favoring tiagabine XR were observed for: 1) change in percent pain relief in the last 24 hours and 2) extent that pain interfered with sleep during the last 24 hours (see FIG. 1). Improvement trends favoring tiagabine XR were observed in all planned BPI variables. All randomized subjects completed the study. In this study, tiagabine XR was safe and demonstrated a consistent trend in pain improvement in patients with diabetic polyneuropathy.

The statistically significant differences ($P \leq 0.05$) during the double-blind phase favoring tiagabine XR were observed for the changes in percent of pain relief that the treatment had provided in the last 24 hours and the extent that pain had interfered with sleep in the last 24 hours. Improvement favoring tiagabine XR, though not statistically significantly different from placebo, were observed in all the other pre-planned BPI variables. The most notable treatment differences occurred in the BPI items pertaining to the extent that pain in the last 24 hours had interfered with relations to people, general activity, enjoyment of life, and mood. Tiagabine XR demonstrated positive effects in both the Dose-Evaluation Period (open-label treatment) and the Double-Blind Phase.

We claim:

1. A method of treating pain associated with diabetic polyneuropathy in a patient in need thereof by administering a pharaceutically effective amount of the compound (R)-N-[4,4Bis(3-methyl-2-thienyl)-3-butenyl]nipecotic acid hydrochloride to said patient.

2. The method of claim 1 wherein said (R)-N-[4,4-Bis(3-methyl-2-thienyl)-3butenyl]nipecotic acid hydrochloride is in an extended release formulation.

* * * * *